(12) United States Patent
Yang et al.

(10) Patent No.: US 10,047,947 B1
(45) Date of Patent: Aug. 14, 2018

(54) SALT LAMP WITH SALT CRYSTAL SUPPORTING ARRANGEMENT

(71) Applicant: ETEKCITY CORPORATION, Anaheim, CA (US)

(72) Inventors: Lin Yang, Shenzhen (CN); Hai Yang, Shenzhen (CN)

( * ) Notice: Subject to any disclaimer, the term of this patent is extended or adjusted under 35 U.S.C. 154(b) by 0 days.

(21) Appl. No.: 15/803,744

(22) Filed: Nov. 4, 2017

(51) Int. Cl.
| | |
|---|---|
| *F21V 33/00* | (2006.01) |
| *F21V 15/01* | (2006.01) |
| *F21V 17/10* | (2006.01) |
| *F21Y 115/10* | (2016.01) |

(52) U.S. Cl.
CPC .......... *F21V 33/0004* (2013.01); *F21V 15/01* (2013.01); *F21V 17/105* (2013.01); *F21Y 2115/10* (2016.08)

(58) Field of Classification Search
CPC ...... A61L 9/03; F21V 33/0004; F21V 17/105; F21V 15/01
See application file for complete search history.

(56) References Cited

U.S. PATENT DOCUMENTS

| | | | | |
|---|---|---|---|---|
| 2005/0030747 A1* | 2/2005 | Bogdal | ...................... | A61L 9/03 |
| | | | | 362/253 |
| 2010/0260491 A1* | 10/2010 | Pitz | ...................... | A01M 1/2061 |
| | | | | 392/390 |
| 2013/0265743 A1* | 10/2013 | Lee | ...................... | F21V 33/0004 |
| | | | | 362/96 |

FOREIGN PATENT DOCUMENTS

DE          29913201 U1 * 11/1999  .......... A61M 11/041

* cited by examiner

*Primary Examiner* — Evan Dzierzynski
(74) *Attorney, Agent, or Firm* — Tsz Lung Yeung

(57) ABSTRACT

A salt lamp includes a main body having a receiving cavity, a first display member having a through slot communicating the receiving cavity with an exterior of the main body, at least one salt crystal member securely supported in the receiving cavity, an illuminating unit, and a salt crystal supporting arrangement. The salt crystal supporting arrangement includes a residual collection tray detachably supported in the receiving cavity at a position underneath the salt crystal member. The a residual collection tray has a supporting portion for partially supporting the salt crystal member, and an indented portion to form a residual storage cavity for storing liquid residual dripping from the salt crystal member.

20 Claims, 4 Drawing Sheets

SALT LAMP WITH SALT CRYSTAL SUPPORTING ARRANGEMENT

BACKGROUND OF THE PRESENT INVENTION

Field of Invention

The present invention relates to a salt lamp, and more particularly to a salt lamp comprising a salt crystal supporting arrangement which is capable of effectively facilitating ionization of salt crystal members and collecting liquid residuals dripping therefrom so as to prolong a general lifespan of the salt lamp of the present invention.

Description of Related Arts

A conventional salt lamp usually comprises a base unit, a predetermined salt rock or a plurality of salt crystals, such as Himalayan salt rock or Himalayan salt crystals, and a light source supported within the salt rock or salt crystals to generate illumination through the salt rock or salt crystals. The illumination generated by the light source may heat up the salt crystal which is then arranged to release negative ions back to ambient air.

There exist several disadvantages in association with the above-mentioned conventional salt lamp. First, conventional salt lamps such as the one mentioned above usually involve making a very confined space in the salt rock that the light source may be embedded in that confined space. The disadvantage is that in this conventional practice, the release of negative ions to ambient air is relatively slow and inefficient.

Furthermore, the residuals of the salt rock in the form of liquid may easily come into contact with the light source which is usually a LED light module comprising mechanical and electrical components. Over time, the liquid residual may cause the LED light module to corrode and stop functioning. In addition, since most of the components are embedded in the salt rock, it would be very difficult to replace or repair when one or more such components is broken.

As a result, there is a need to develop a salt lamp which may improve upon the above-mentioned conventional salt lamps and may deliver negative ions and illumination in an efficient and reliable manner.

SUMMARY OF THE PRESENT INVENTION

Certain variations of the present invention provide a salt lamp comprising a salt crystal supporting arrangement which is capable of effectively facilitating ionization of salt crystal members and collecting liquid residuals dripping therefrom so as to prolong a general lifespan of the salt lamp of the present invention.

Certain variations of the present invention provide a salt lamp which comprises a residual collection tray which is capable of collecting liquid residual from at least one salt crystal member and preventing liquid residual from undesirably reaching other components of the salt lamp.

In one aspect of the present invention, it provides a salt lamp, comprising:

a main body having a bottom wall, a sidewall extended from the bottom wall, and a receiving cavity;

a first display member attached on the main body to substantially cover the receiving cavity, the first display member having a first through slot communicating the receiving cavity with an exterior of the main body;

at least one salt crystal member securely supported in the receiving cavity;

an illuminating unit securely supported in the receiving cavity; and a salt crystal supporting arrangement, which comprises:

a residual collection tray detachably supported in the receiving cavity at a position underneath the salt crystal member, the residual collection tray having a supporting portion for partially supporting the salt crystal member, and an indented portion to form a residual storage cavity for storing liquid residual dripping from the salt crystal member.

This summary presented above is provided merely to introduce certain concepts and not to identify any key or essential features of the claimed subject matter.

DETAILED DESCRIPTION OF THE PREFERRED EMBODIMENT

Figure 1:
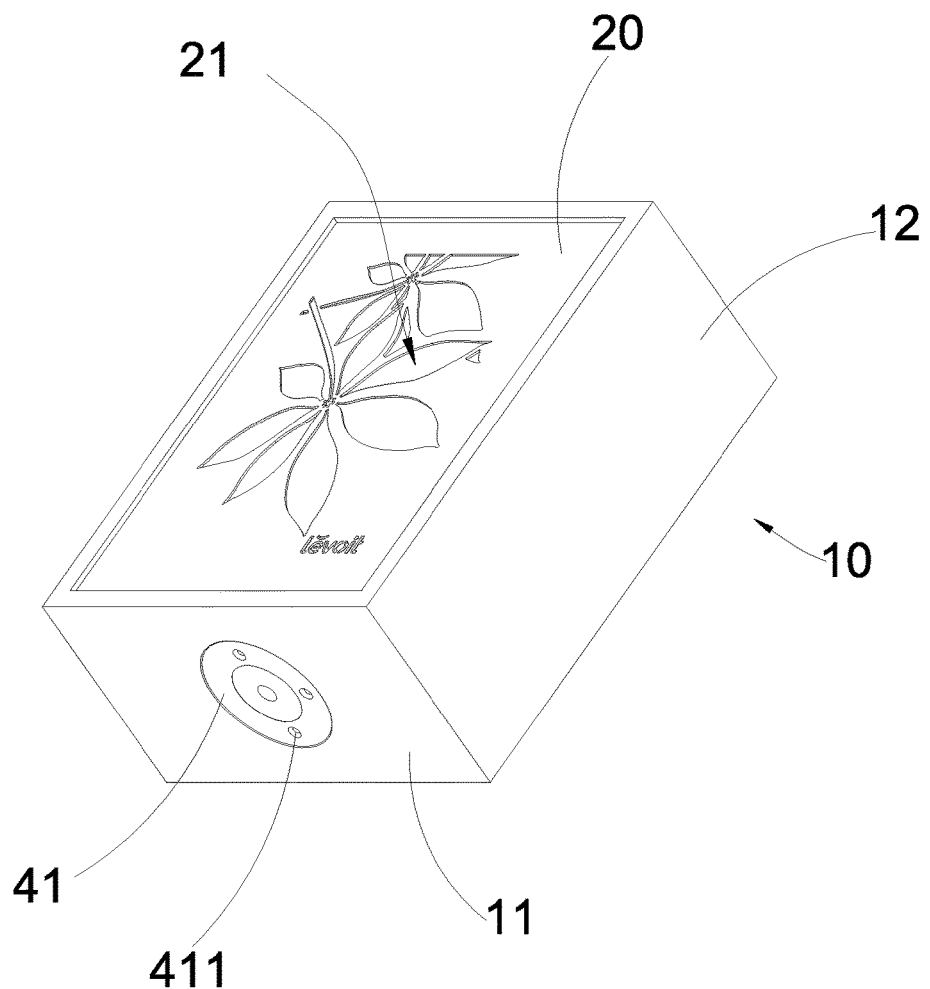
FIG. 1 is a perspective view of a salt lamp according to a preferred embodiment of the present invention.
Figure 2:
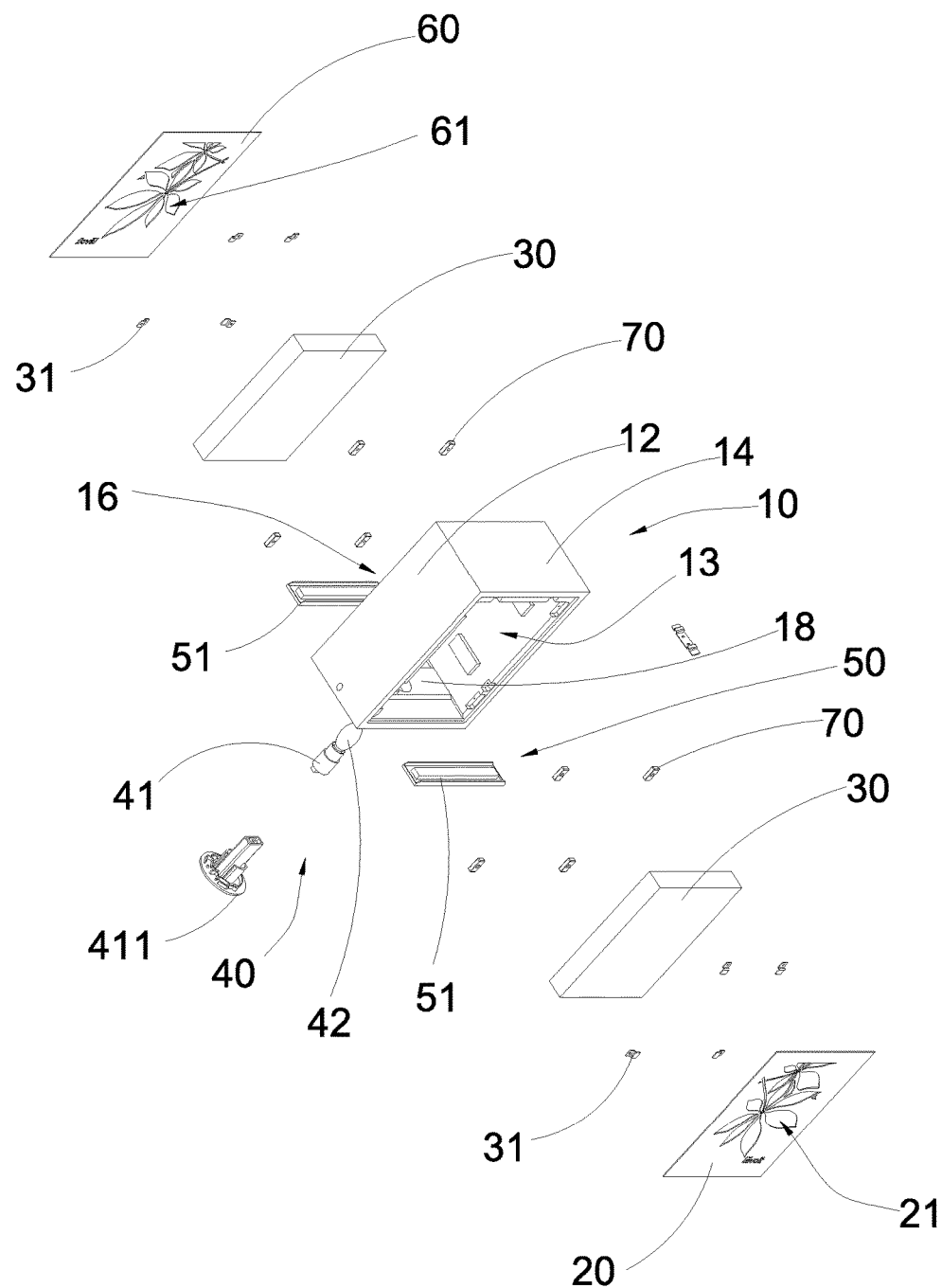
FIG. 2 is an exploded perspective view of the salt lamp according to the preferred embodiment of the present invention.

The following detailed description of the preferred embodiment is the preferred mode of carrying out the invention. The description is not to be taken in any limiting sense. It is presented for the purpose of illustrating the general principles of the present invention.

Referring to FIG. 1 to FIG. 4 of the drawings, a salt lamp according a preferred embodiment of the present invention is illustrated. Broadly, the salt lamp may comprise a main body 10, a first display member 20, at least one salt crystal member 30, an illuminating unit 40, and a salt crystal supporting arrangement 50. The salt lamp may be utilized to deliver a predetermined amount of illumination and negative ions to ambient air.

The main body 10 may have a bottom wall 11, at least one sidewall 12 extended from the bottom wall 10 and a receiving cavity 13.

The first display member 20 may be attached on the main body 10 (preferably on a front side) to substantially cover the receiving cavity 13. The first display member 20 may have at least one first through slot 21 communicating the receiving cavity 13 with an exterior of the main body 10. The salt crystal member 30 may be securely supported in the receiving cavity 13. The illuminating unit 40 may also be securely supported in the receiving cavity 13.

The salt crystal supporting arrangement 50 may comprise a residual collection tray 51 detachably supported in the receiving cavity 13 at a position underneath the salt crystal member 30. The residual collection tray 51 may have a supporting portion 511 for partially supporting the salt crystal member 30, and an indented portion 512 to form a residual storage cavity 513 for storing liquid residual dripping from the salt crystal member 30.

Figure 3:
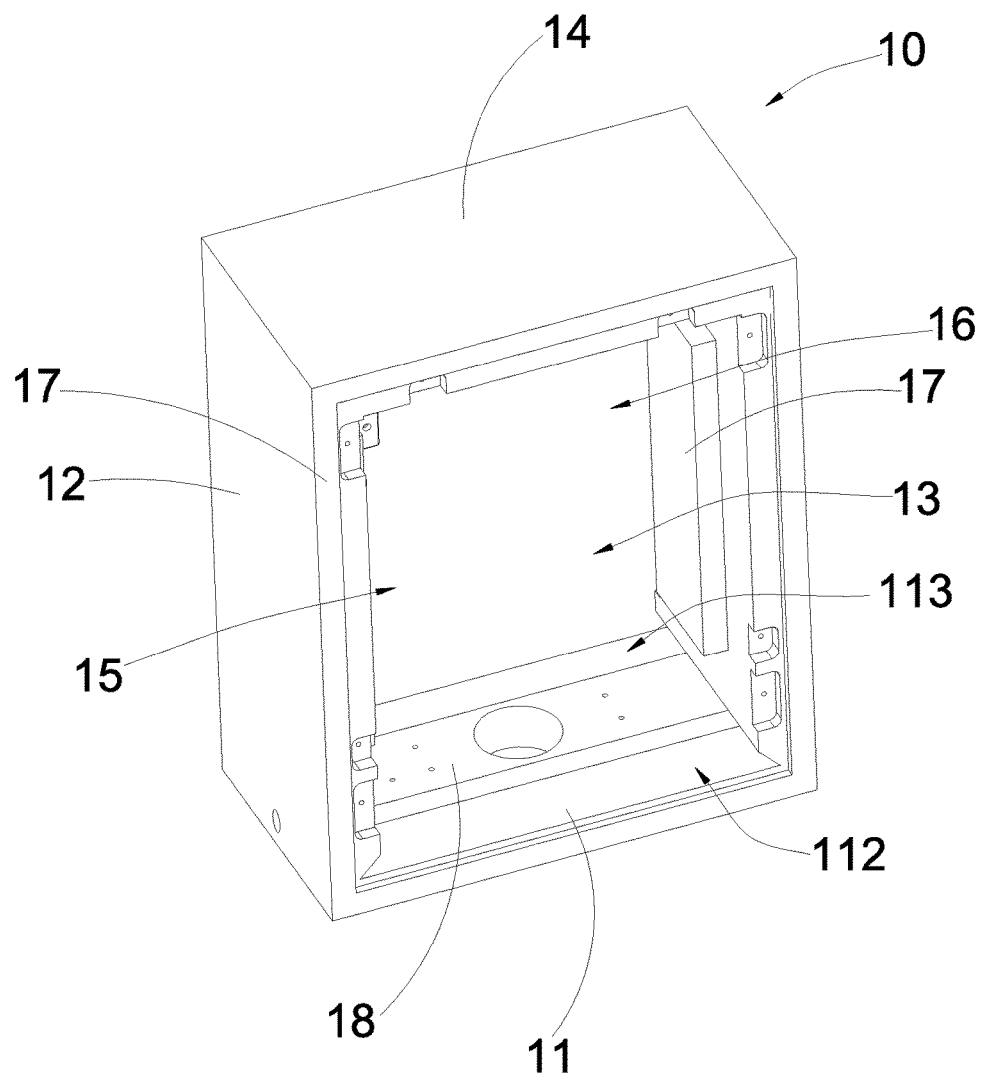
FIG. 3 is a partially exploded perspective view of the salt lamp according to the preferred embodiment of the present invention.

According to the preferred embodiment of the present invention, the main body 10 may be configured as having a cubic or rectangular structure and may comprise the bottom wall 11, a top wall 14, and two sidewalls 12 extended between the bottom wall 10 and the top wall 14. The receiving cavity 13 may be formed as a space between the top wall 14, the bottom wall 11 and the two sidewalls 12. A front opening 15 and a rear opening 16 may be formed for communicating the receiving cavity 13 with an exterior of the main body 10 (as shown in FIG. 3 of the drawings). Each of the top wall 14, the bottom wall 11 and the sidewalls 12 may be configured as having a rectangular shape. Of course, other shapes are also possible. The main body 10 may also be configured as having other structural contours, such as cubic, cylindrical or even spherical.

The first display member 20 may be attached on the main body 10 on a front side thereof to substantially cover the front opening 15. The first display member 20 may also have a rectangular cross-sectional shape which corresponds to that of the front opening 15. On the other hand, the salt lamp may further comprise a second display member 60 attached on a rear side of the main body 10 for substantially covering the rear opening 16 thereof. The second display member 60 may also have a rectangular cross-sectional shape which corresponds to that of the rear opening 16. Each of the first display member 20 and the second display member 60 may be configured as having a panel structure.

The second display member 60 may have a second through slot 61 formed thereon, so that when the second display member 60 is attached on the rear side of the main body 10, visual and physical communication between the receiving cavity 13 and the exterior of the main body 10 may also be accomplished through the second through slot 61. In this preferred embodiment, the main body 10 may be made of or configured from wood material. Of course, other material for making the main body 10 may also be possible. The first display member 20 and the second display member 60 may be configured from magnetic material or ferromagnetic material, such as iron.

It is worth mentioning that the first display member 20 and the second display member 60 may have a plurality of first through slots 21 and the second through slots 61 wherein the first through slots 21 and the second through slots 61 may be shaped and crafted to form aesthetically appealing designs on the respective first display member 20 and the second display member 60. These aesthetically appealing designs may be visually apparent when the illuminating unit 40 is operating and may impart a relaxing visual effect to a user of the salt lamp of the present invention.

The salt lamp may further comprise a plurality of magnets 70 securely attached on the main body 10 for magnetically attracting the first display member 20 and the second display member 60 on the main body 10. Thus, a user may be able to convenient attach or detach the first display member 20 or the second display member 60 to or from the main body 10 for repairing components or replacing the salt crystal members 30 or for cleaning the residual collection tray 51 (i.e. accessing the receiving cavity 13).

The salt lamp of the present invention may comprise two salt crystal members 30 securely supported in the receiving cavity 13. As shown in FIG. 3 of the drawings, the two salt crystal members 30 may be detachably supported adjacent to the first display member 20 and the second display member 60 respectively. Each of the salt crystal members 30 may be configured as a salt rock and having a rectangular structure. The two salt crystal members 30 may be light admissible so that illumination may pass from the receiving cavity 13 to an exterior of the main body 10 through the salt crystal members 30 and the through slots 21 (61).

The illuminating unit 40 may comprise a mounting frame 41 and an illuminator 42 detachably attached on the mounting frame 41 for providing illumination in the receiving cavity 13. Specifically, the mounting frame 41 may be attached on the bottom wall 11 of the main body 10 and accommodated in the receiving cavity 13 at a position between the two salt crystal members 30. The mounting frame 41 may have an electrical port 411 adapted for connecting to an external power source, such as an external AC power source, for providing power to the illuminator 42.

Figure 4:
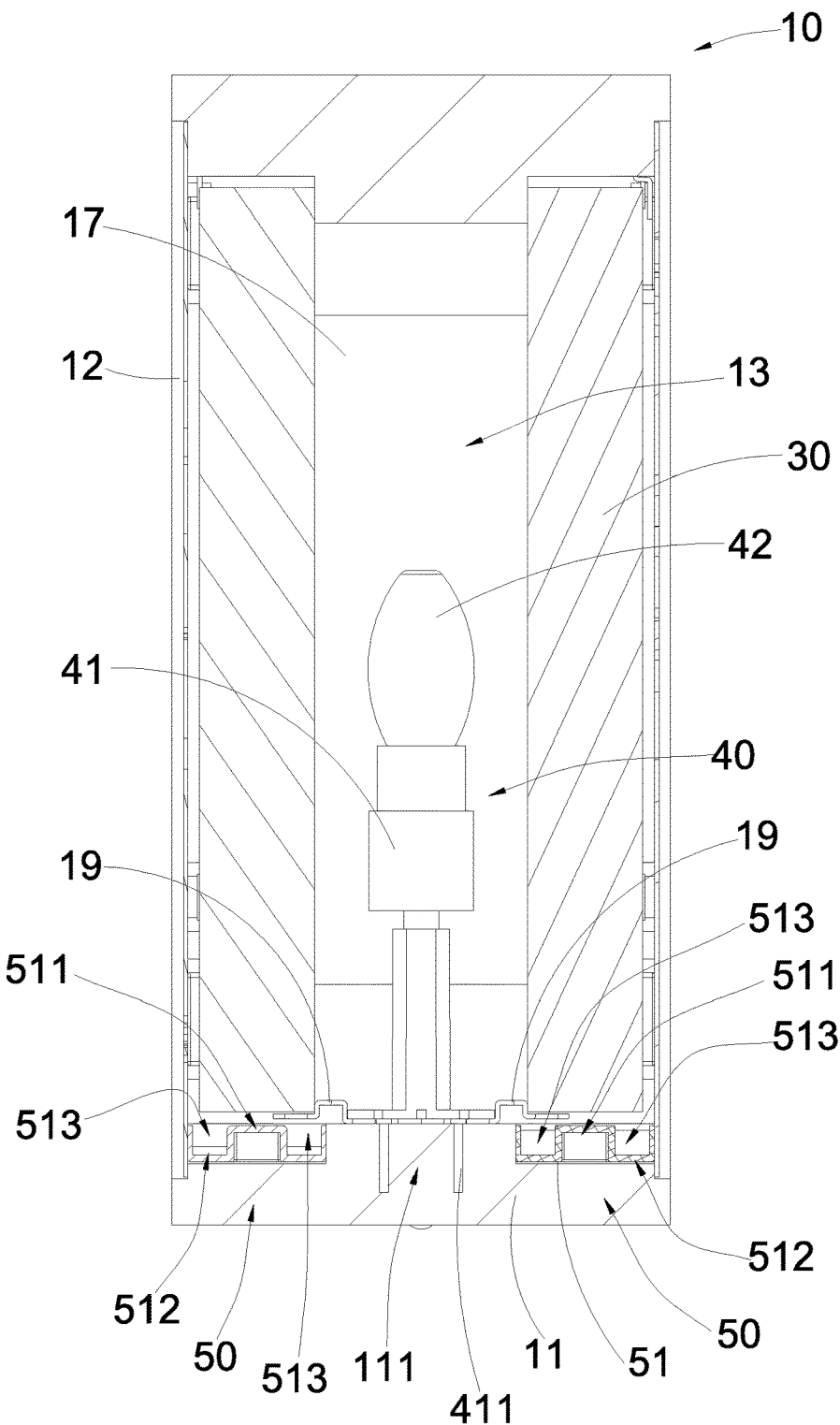
FIG. 4 is a schematic side view of the salt lamp according to the preferred embodiment of the present invention.

As shown in FIG. 4 of the drawings, the illuminator 42 may be upwardly extended from the mounting frame 41 and may be provided in the receiving cavity 13 at a position between the two salt crystal members 30. The illuminator 42 may be configured as a LED light bulb which is capable of generating illumination toward the salt crystal members 30. The illumination may then pass through the salt crystal members 30 and reach the exterior of the main body 10 through the first through slot 21 and the second through slot 61.

The salt crystal supporting arrangement 50 may further comprise one residual collection tray 51 so that the salt lamp of the present invention may comprise altogether two residual collection trays 51. The residual collection trays 51 may be detachably attached on the bottom wall 11 of the main body 10 and may be positioned underneath the salt crystal members 30 respectively for partially supporting the salt crystal members 30 and for collecting liquid residual from the salt crystal members 30.

Each of the residual collection trays 51 may be structurally identical. Specifically, each of the residual collection trays 51 may have a supporting portion 511, and two indented portions 512 formed on two sides of the supporting portion 511 respectively. Each of the indented portions 512 may form the residual storage cavity 513 for temporarily storing the liquid residual from the corresponding salt crystal members 30. Thus, as shown in FIG. 4 of the drawings, each of the indented portions 512 may have a U-shaped cross section for forming the residual storage cavity 513, as shown in FIG. 4 of the drawings. Moreover, a maximum vertical height of the supporting portions 511 may be higher than that of the corresponding indented portions 512 with respect to the bottom wall 11.

The salt crystal members 30 may be supported by the supporting portions 511 of the residual collection trays 51 respectively. In addition, the salt crystal members 30 may also be attached on the sidewalls 12 of the main body 10 through a plurality of connectors 31 respectively. The connectors 31 may provide support to the salt crystal members 30 from the side while the supporting portions 511 may provide support to the salt crystal members 30 from the bottom.

On the other hand, the main body 10 may further comprise a plurality of securing members 19 provided on a front portion 112 and a rear portion 113 of the bottom wall 11 of the main body 10 respectively for securing bottom portions of the salt crystal members 30 to the bottom wall 11. A width of each of the securing members 19 may be less than that of the corresponding front portion 112 and the rear portion 113 of the bottom wall 11.

Referring to FIG. 3 and FIG. 4 of the drawings, the main body 10 may further comprise a plurality of blocking members 17 connected to the sidewalls 12 respectively. Each of the blocking members 17 may be positioned between the salt crystal members 30 so as to act as a stopper for preventing the salt crystal members 30 from accidentally collapsing on the illuminating unit 40. In this preferred embodiment, each of the blocking members 17 may be configured as a rectangular wooden block. Other variations may also be possible. For example, the blocking member 17 may be embodied as a pin, a latch, or other forms of stoppers.

The main body 10 may further comprise a protection platform 18 upwardly extended from a mid portion 111 of the bottom wall 11, wherein the mounting frame 41 of the illuminating unit 40 may be secured on the protection platform 18 so that the mounting frame 41 may be secured in the receiving cavity 13 at a predetermined elevation dictated by a height of the protection platform 18. A vertical height of the protection platform 18 may be higher than a vertical depth of the indented portions 512 of the residual collection tray 51 so that the liquid residuals collected in the indented portions 512 may be prevented from reaching the illuminating unit 40.

The operation of the present invention is as follows: the illuminating unit 40 may be electrically connected to an external power source, such as an AC power source. When the illuminator 42 is turned on, the illumination may be observed from an exterior of the main body 10 through the first through slot 21 and the second through slot 61. At the same time, the salt crystal members 30 is arranged to melt very slowly. Negative ions are generated and released to ambient air through the first through slot 21 and the second through slot 61. Liquid residuals will then drip into the residual collection trays 51. Because of the special construction of the residual collection tray 51, the liquid residuals will be collected in the residual storage cavity 513 of the corresponding residual collection tray 51. A user may be able to detach the first display member 20 and the second display member 60 from the main body 10 for detaching the residual collection trays 51 from the main body 10. After that, the user may clean the residual collection trays 51 and put them back for future use.

The present invention, while illustrated and described in terms of a preferred embodiment and several alternatives, is not limited to the particular description contained in this specification. Additional alternative or equivalent components could also be used to practice the present invention.

What is claimed is:

1. A salt lamp, comprising:
a main body having a bottom wall, a sidewall extended from said bottom wall, and a receiving cavity;
a first display member attached on the main body to substantially cover said receiving cavity, said first display member having a first through slot communicating said receiving cavity with an exterior of said main body;
at least one salt crystal member securely supported in said receiving cavity;
an illuminating unit securely supported in said receiving cavity; and
a salt crystal supporting arrangement, which comprises:
a residual collection tray detachably supported in said receiving cavity at a position underneath said salt crystal member, said residual collection tray having a supporting portion for partially supporting said salt crystal member, and an indented portion to form a residual storage cavity for storing liquid residual dripping from said salt crystal member.

2. The salt lamp, as recited in claim 1, further comprising a second display member attached on a rear side of said main body for substantially covering said rear opening thereof, said second display member having a second through slot formed thereon for communicating said receiving cavity with an exterior of said main body.

3. The salt lamp, as recited in claim 2, wherein said main body further comprises a top wall and a sidewall, said sidewalls extending between said bottom wall and said top wall, said receiving cavity being formed as a space between said top wall, said bottom wall and said two sidewalls, said main body having a front opening and a rear opening as two openings of said receiving cavity for communicating said receiving cavity with an exterior of said main body.

4. The salt lamp, as recited in claim 3, further comprising a salt crystal member, said salt crystal members being supported on two sidewalls of said main body in said receiving cavity at positions adjacent to said first display member and said second display member respectively, said two salt crystal members being configured as light admissible so that illumination from said receiving cavity is capable of reaching an exterior of said main body through said salt crystal members and said first through slot and said second through slot.

5. The salt lamp, as recited in claim 4, further comprising a residual collection tray, said two residual collection trays being structurally identical and provided underneath said two salt crystal members respectively.

6. The salt lamp, as recited in claim 5, wherein said illuminating unit comprises a mounting frame and an illuminator detachably attached on said mounting frame for providing illumination in said receiving cavity, said mounting frame being supported on said bottom wall of said main body and accommodated in said receiving cavity at a position between said two salt crystal members, said mounting frame having an electrical port for connecting to an external power source.

7. The salt lamp, as recited in claim 6, wherein said illuminator is upwardly extended from said mounting frame and is provided in said receiving cavity at a position between said two salt crystal members.

8. The salt lamp, as recited in claim 7, wherein each of said residual collection trays has a supporting portion, and two indented portions formed on two sides of said supporting portion respectively, each of said indented portions form said residual storage cavity for temporarily storing said liquid residual from said corresponding salt crystal members, a maximum vertical height of said supporting portion being higher than that of said corresponding indented portions with respect to said bottom wall.

9. The salt lamp, as recited in claim 8, wherein said main body further comprises a plurality of securing members provided on a front portion and a rear portion of said bottom wall of said main body respectively for securing bottom portions of said salt crystal members to said bottom wall.

10. The salt lamp, as recited in claim 9, wherein said main body further comprises a protection platform upwardly extended from a mid portion of said bottom wall, said mounting frame of said illuminating unit being secured on said protection platform so that said mounting frame is secured in said receiving cavity at a predetermined elevation dictated by a height of said protection platform, a vertical height of said protection platform being higher than a vertical depth of said indented portions of said residual collection trays with respect to said bottom wall so that said liquid residuals collected in said indented portions is prevented from reaching said illuminating unit.

11. The salt lamp, as recited in claim 10, wherein said first display member being attached on a front side of said main body for substantially covering said front opening thereof, said second display member being attached on a rear side of said main body for substantially covering said rear opening thereof.

12. The salt lamp, as recited in claim 11, wherein at least one of said first display member and said second display member being configured from ferromagnetic material.

13. The salt lamp, as recited in claim 12, further comprising a plurality of magnets securely attached on said main body for magnetically and detachably attracting said first display member and said second display member on said main body.

14. The salt lamp, as recited in claim 13, wherein said main body further comprises a plurality of blocking members connected to said sidewalls respectively, each of said blocking members being positioned between said salt crystal members 30 so as to act as a stopper for preventing said salt crystal member from accidentally collapsing on said illuminating unit.

15. The salt lamp, as recited in claim 3, wherein said first display member being attached on a front side of said main body for substantially covering said front opening thereof, said second display member being attached on a rear side of said main body for substantially covering said rear opening thereof.

16. The salt lamp, as recited in claim 15, wherein at least one of said first display member and said second display member being configured from ferromagnetic material.

17. The salt lamp, as recited in claim 16, further comprising a plurality of magnets securely attached on said main body for magnetically and detachably attracting said first display member and said second display member on said main body.

18. The salt lamp, as recited in claim 3, wherein said main body further comprises a plurality of blocking members connected to said sidewalls respectively, each of said blocking members being positioned between said salt crystal members 30 so as to act as a stopper for preventing said salt crystal member from accidentally collapsing on said illuminating unit.

19. The salt lamp, as recited in claim 8, wherein said main body further comprises a plurality of blocking members connected to said sidewalls respectively, each of said blocking members being positioned between said salt crystal members 30 so as to act as a stopper for preventing said salt crystal member from accidentally collapsing on said illuminating unit.

20. The salt lamp, as recited in claim 12, wherein said main body further comprises a plurality of blocking members connected to said sidewalls respectively, each of said blocking members being positioned between said salt crystal members 30 so as to act as a stopper for preventing said salt crystal member from accidentally collapsing on said illuminating unit.

* * * * *